US012387746B2

(12) United States Patent
Baruchi (10) Patent No.: US 12,387,746 B2
(45) Date of Patent: Aug. 12, 2025

(54) SYSTEMS AND METHODS FOR DETECTING COGNITIVE CHANGE BASED ON VOICE AND SMARTPHONE SENSORS

(71) Applicant: MYNDYOU INTERNATIONAL HOLDINGS LTD., Tel Aviv (IL)

(72) Inventor: Itay Baruchi, Tel Aviv-Jaffa (IL)

(73) Assignee: MYNDYOU INTERNATIONAL HOLDINGS LTD., Tel Aviv (IL)

( * ) Notice: Subject to any disclaimer, the term of this patent is extended or adjusted under 35 U.S.C. 154(b) by 396 days.

(21) Appl. No.: 17/619,606

(22) PCT Filed: Jun. 17, 2020

(86) PCT No.: PCT/IL2020/050667
§ 371 (c)(1),
(2) Date: Dec. 16, 2021

(87) PCT Pub. No.: WO2020/255127
PCT Pub. Date: Dec. 24, 2020

(65) Prior Publication Data
US 2022/0301581 A1    Sep. 22, 2022

Related U.S. Application Data

(60) Provisional application No. 62/863,536, filed on Jun. 19, 2019.

(51) Int. Cl.
*G10L 25/30* (2013.01)
*A61B 5/00* (2006.01)
(Continued)

(52) U.S. Cl.
CPC .............. *G10L 25/66* (2013.01); *G10L 25/30* (2013.01); *G10L 25/93* (2013.01)

(58) Field of Classification Search
CPC .......... G10L 25/66; G10L 25/30; G10L 25/93
See application file for complete search history.

(56) References Cited

U.S. PATENT DOCUMENTS 9,516,442 B1 *   12/2016   Dusan ................. H04R 1/1016
2015/0112899 A1 *   4/2015   Dagum ................. A61B 5/163
706/12

(Continued)

FOREIGN PATENT DOCUMENTS

CN    109493968    3/2019
JP     4876207     2/2012

(Continued)

OTHER PUBLICATIONS

Grünerbl, Agnes, et al. "Smartphone-based recognition of states and state changes in bipolar disorder patients." IEEE journal of biomedical and health informatics 19.1 (2014): 140-148. (Year: 2014).*

(Continued)

*Primary Examiner* — Jialong He
(74) *Attorney, Agent, or Firm* — PEARL COHEN ZEDEK LATZER BARATZ LLP (57) ABSTRACT

Generally, systems and methods for determining a change of a cognitive capability of a user are disclosed. The method may include: receiving at least one sensor signal acquired by at least one sensor (such as an accelerometer, gyro and/or magnetometer) mounted within a mobile phone of the user; determining a voice activity dataset based on the at least one sensor signal; and determining a change of a cognitive capability of the user based on the voice activity dataset. Advantageously, the disclosed systems and methods may enable determining anomalies and trends in the cognition of the user based on the sensor(s) mounted within the mobile phone of the user, without collecting and/or recording the voice of the user.

8 Claims, 7 Drawing Sheets

(51) Int. Cl.
  *G10L 25/18* (2013.01)
  *G10L 25/66* (2013.01)
  *G10L 25/93* (2013.01)

(56) References Cited

U.S. PATENT DOCUMENTS

| | | | | |
|---|---|---|---|---|
| 2019/0167179 | A1* | 6/2019 | Arzy | A61B 5/7475 |
| 2019/0272842 | A1* | 9/2019 | Bryan | G10L 21/0272 |
| 2021/0000411 | A1* | 1/2021 | Nagumo | G10L 25/66 |

FOREIGN PATENT DOCUMENTS

| | | | |
|---|---|---|---|
| JP | 4876207 B2 | * | 2/2012 |
| JP | 2017196115 | | 11/2017 |

OTHER PUBLICATIONS

Majumder, Sumit, and M. Jamal Deen. "Smartphone sensors for health monitoring and diagnosis." Sensors 19.9 (May 2019): 2164. (Year: 2019).*

Fangmeng, Zeng, et al. "Emotional changes detection for dementia people with spectrograms from physiological signals." International Journal of Advanced Computer Science and Applications 9.10 (2018). (Year: 2018).*

Martínez-Sánchez, Francisco, et al. "A prototype for the voice analysis diagnosis of Alzheimer's disease." Journal of Alzheimer's disease 64.2 (2018): 473-481. (Year: 2018).*

Caielli, Matteo. "Automatic speech analysis for early detection of functional cognitive impairment in elderly population." (2018) (Year: 2018).*

Aleksandar Matic; Speech Activity Detection using Accelerometer, 34th Annual International Conference of the IEEE EMBS San Diego, California USA, Aug. 28-Sep. 1, 2012, Sep. 1, 2012 (Sep. 1, 2012).

Li, S. C. X., & Marlin, B. M. (2016). A scalable end-to-end gaussian process adapter for irregularly sampled time series classification. In Advances in neural information processing systems (pp. 1804-1812).

VanderPlas, J. T. (2018). Understanding the lomb-scargle periodogram. The Astrophysical Journal Supplement Series, 236(1), 16.

Murray, G. M. (1994). The Quark and the Jaguar: Adventures in the Simple and the Complex. Yang, JY, Ed, 5-7.

Ben-Jacob, E. (2003). Bacterial self-organization: co-enhancement of complexification and adaptability in a dynamic environment. Philosophical Transactions of the Royal Society of London. Series A: Mathematical, Physical and Engineering Sciences, 361(1807), 1283-1312.

International Search Report of Application No. PCT/IL2020/050667 mailed on Aug. 6, 2020.

* cited by examiner

SYSTEMS AND METHODS FOR DETECTING COGNITIVE CHANGE BASED ON VOICE AND SMARTPHONE SENSORS

CROSS-REFERENCE TO RELATED APPLICATIONS

This application is a National Phase Application of PCT International Application No. PCT/IL2020/050667, International Filing Date Jun. 17, 2020, claiming the benefit of U.S. Provisional Patent Application No. 62/863,536, filed Jun. 19, 2019, which are hereby incorporated by reference.

FIELD OF THE INVENTION

The present invention relates to the field of detecting cognitive change and, more particularly, to detecting cognitive change based on voice and smartphone sensors.

BACKGROUND OF THE INVENTION

A voice pattern of a human may be affected by a change in the human's cognitive capabilities. Collection of voice data may be restricted due to privacy and/or technical obstacles.

SUMMARY OF THE INVENTION

Some embodiments of the present invention may provide a system for determining a change of a cognitive capability of a user, the system may include: a storage module configured to receive at least one sensor signal acquired by at least one sensor during a phone conversation of the user, wherein the at least one sensor is mounted within a mobile phone of the user and selected from a group consisting of: an accelerometer, gyro and magnetometer; a voice activity determination module configured to determine a voice activity dataset based on the at least one sensor signal, wherein the voice activity dataset comprises a plurality of data values each representing a specific time window and indicating a voice detection or an absence thereof at the time window thereof; and a cognitive capability determination module configured to determine a change of a cognitive capability of the user based on the voice activity dataset.

In some embodiments, the system further comprising a voice complexity determination module configured to determine a voice complexity based on the voice activity dataset.

In some embodiments, the cognitive capability determination module is configured to determine the change of the cognitive capability of the user based on the voice complexity.

In some embodiments, the at least one sensor signal is acquired upon a verification that the user speaks directly to the mobile phone during the phone conversation.

In some embodiments, the voice activity determination module is further configured to determine a plurality of sensor signal segments based on the at least one sensor signal and to determine the voice activity dataset based on the plurality of sensor signal segments using a machine learning algorithm.

In some embodiments, the voice activity determination module is further configured to determine a time-frequency domain representation of each of the plurality of sensor signal segments to yield a plurality of time-frequency domain representations, and the cognitive capability determination module is further configured to determine the voice activity dataset based on the plurality of the time-frequency domain representations using the machine learning algorithm.

Some embodiments of the present invention may provide a method of determining a change of a cognitive capability of a user, the method may include: receiving at least one sensor signal acquired by at least one sensor during a phone conversation of the user, wherein the at least one sensor is mounted within a mobile phone of the user and selected from a group consisting of: an accelerometer, gyro and magnetometer; determining a voice activity dataset based on the at least one sensor signal, wherein the voice activity dataset comprises a plurality of data values each representing a specific time window and indicating a voice detection or an absence thereof at the time window thereof; and determining a change of a cognitive capability of the user based on the voice activity dataset.

In some embodiments, the method may include determining a voice complexity based on the voice activity dataset.

In some embodiments, the method may include determining the change of the cognitive capability of the user based on the voice complexity.

In some embodiments, the method may include acquiring the at least one sensor signal upon a verification that the user speaks directly to the mobile phone during the phone conversation.

In some embodiments, the method may include determining a plurality of sensor signal segments based on the at least one sensor signal and determining the voice activity dataset based on the plurality of sensor signal segments using a machine learning algorithm.

In some embodiments, the method may include determining a time-frequency domain representation of each of the plurality of sensor signal segments to yield a plurality of time-frequency domain representations, and determining the voice activity dataset based on the plurality of the time-frequency domain representations using the machine learning algorithm.

These, additional, and/or other aspects and/or advantages of the present invention are set forth in the detailed description which follows, possibly inferable from the detailed description, and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Some embodiments of the present invention may provide systems and methods for determining a change of a cognitive capability of a user based on voice and based on sensors mounted within a mobile phone of the user.

The system may be configured to receive at least one sensor signal acquired by at least one sensor mounted within the mobile phone of the user, wherein the sensor(s) is not a microphone. For example, the sensor(s) may be an accelerometer, a gyro and/or a magnetometer. The system may be configured to determine a voice activity dataset for the user based on the sensor signals.

The system may be configured to determine one or more changes in the voice activity dataset determined for the user (e.g., as compared to a user-specific reference voice activity dataset associated with the user) that may be indicative of the change of the cognitive capability of the user.

Advantageously, the disclosed systems and methods may enable determining anomalies and trends in the cognition of the user based on the sensor(s) mounted within the mobile phone of the user, without collecting and/or recording the voice of the user.

Figure 1:
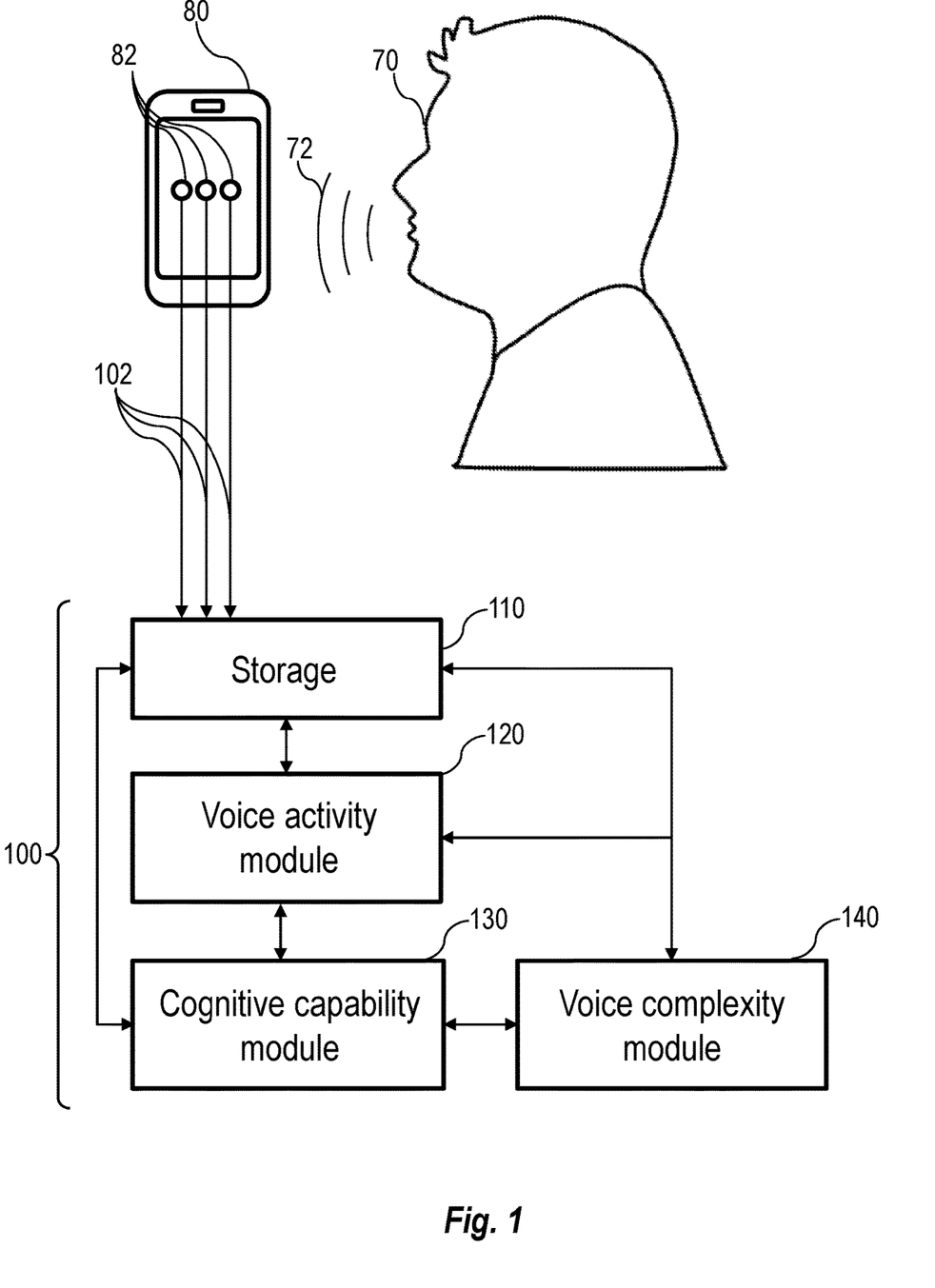
FIG. 1 is a system for determining a change of a cognitive capability of a user, according to some embodiments of the invention.

Reference is now made to FIG. 1, which is a system 100 for determining a change of a cognitive capability of a user, according to some embodiments of the invention.

According to some embodiments, system 100 may include a storage module 110 and a voice activity determination module 120 (e.g., as shown in FIG. 1).

According to some embodiments, storage module 110 may be configured to receive and store at least one sensor signal 102 from at least one sensor 82.

Sensor(s) 82 may be mounted within, for example, a mobile phone 80 of a user 70. Sensor(s) 82 may be any sensor the readings of which may be affected by a voice 72 of user 70. In some embodiments, sensor(s) 82 may be any sensor the readings of which may be affected by movement of a face/head of user 70 during a conversion of user 70 using mobile phone 80. In various embodiments, sensor(s) 82 may be selected from a group of sensors consisting of: an accelerometer, gyro and/or magnetometer. In some embodiments, the group of sensors excludes microphone (e.g., meaning that sensor(s) 82 are not microphone(s)).

Sensor signal(s) 102 may be acquired by sensor(s) 82 during, for example, a phone conversation of user 70 using mobile phone 80. In some embodiments, sensor signal(s) 102 may be acquired when user 70 speaks directly into mobile phone 80 (without using headsets, etc.). In these embodiments, mobile phone 80 of user 70 may be configured to verify that user 70 speaks directly into mobile phone 80 and to acquire sensor signal(s) 102 only upon the verification thereof (e.g., as described below with respect to FIG. 2).

According to some embodiments, system 100 may include a phone case for mobile phone 82. The phone case may include one or more sensors the readings of which may be affected by a voice 72 of user 70 and that are not microphone (such as sensor(s) 82) and, optionally, a power source to supply power to the sensors.

According to some embodiments, voice activity determination module 120 may be in communication with storage module 110.

Voice activity determination module 120 may be configured to determine a voice activity dataset for user 70 based on sensor signal(s) 102 (e.g., as described below with respect to FIG. 3A). The voice activity dataset may include a plurality of data values. Each of the data values of the voice activity dataset may represent a specific time window (e.g., a time window during the phone conversation) and indicate a voice detection or an absence thereof at the specific time window.

According to some embodiments, system 100 may include a cognitive capability determination module 130. Cognitive capability determination module 130 may be in communication with voice activity determination module 120. Cognitive capability determination module 130 may be configured to determine a change of a cognitive capability of user 70 based on the voice activity dataset determined for user 70 (e.g., as described below with respect to FIG. 4).

The change of cognitive capability of a user may be a change in an ability of a person to encode information in addition to the words themselves. The encoded information may be reflected in, for example, less dynamical patterns of pitch, power and pauses between words—e.g., less complex voice patterns.

According to some embodiments, system 100 may include a voice complexity determination module 140. Voice complexity determination module 140 may be in communication with voice activity determination module 120 and/or cognitive capability determination module 130.

Voice complexity determination module 140 may be configured to determine a voice complexity of user 70 based on the voice activity dataset determined for user 70.

The voice complexity may, for example, represent an ability of user 70 to dynamically change voice patterns by changing the voice pitch, power and space between syllables and/or words. The voice complexity may allow conveying addition information (e.g., in addition to the information conveyed by the words themselves) such as, for example, pausing before a word for emphasis, etc. For example, cognitive change typically reduces the ability of user 70 to dynamically change its voice patterns which is reflected in reduction of user's 70 voice complexity.

In some embodiments, cognitive capability determination module 130 may be configured to determine the change of the cognitive capability of user 70 based on the voice complexity determined for user 70 (e.g., as described below with respect to FIG. 5).

According to various embodiments, each of storage module 110, voice activity determination module 120, cognitive capability determination module 130 and voice complexity determination module 140 may be implemented on its own computing device, a single computing device, or a combination of computing devices.

In various embodiments, each of storage module 110, voice activity determination module 120, cognitive capability determination module 130 and voice complexity determination module 140 may be implemented on a server, a cloud, a personal computer, a mobile phone of a user or a combination thereof.

In various embodiments, the communication between storage module 110, voice activity determination module 120, cognitive capability determination module 130 and voice complexity determination module 140 may be wired or wireless.

Figure 2:
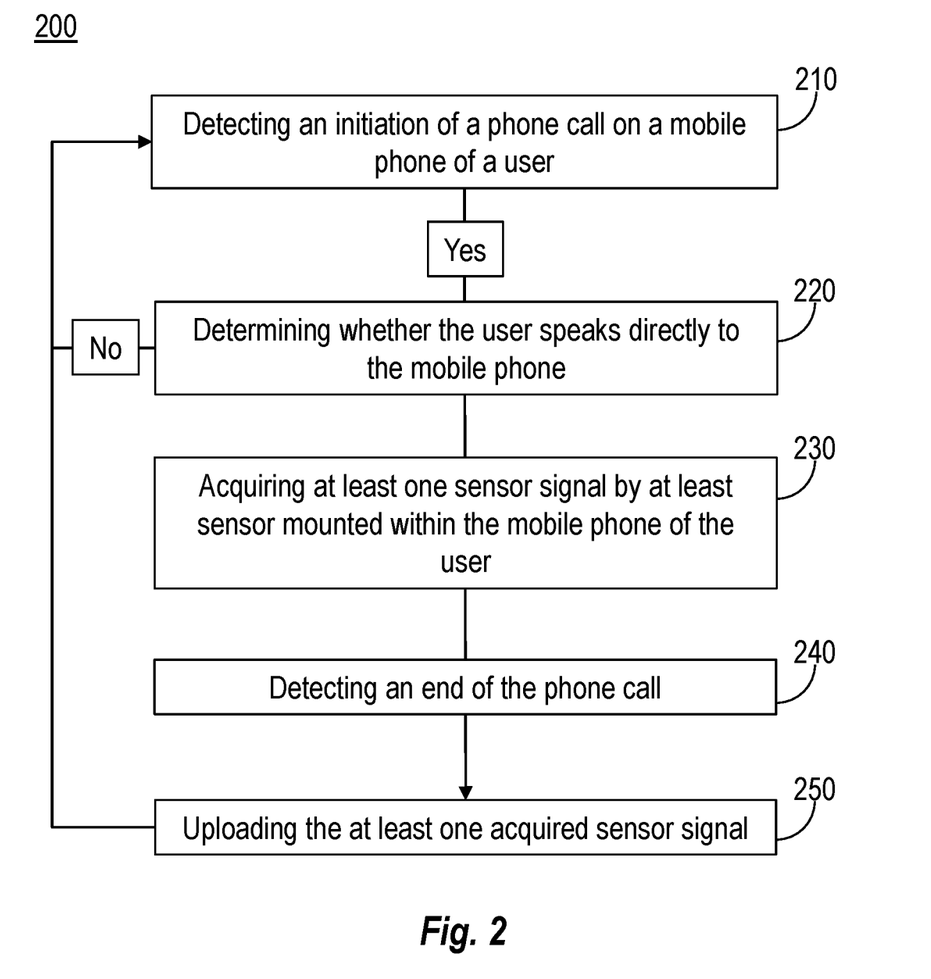
FIG. 2 is a flowchart of a method of acquiring at least one sensor signal by at least one sensor mounted within a mobile phone of a user, according to some embodiments of the invention.

Reference is now made to FIG. 2, which is a flowchart of a method 200 of acquiring at least one sensor signal by at least one sensor mounted within a mobile phone of a user, according to some embodiments of the invention.

Method 200 may be implemented by a mobile phone of a user, which may be configured to implement method 200. For example, the mobile phone may include a computer processor and non-transitory computer readable medium, wherein the non-transitory computer readable medium may include one or more sets of instructions that when executed cause the computer processor to implement functions/acts described with respect to FIG. 2.

According to some embodiments, method 200 may include detecting an initiation of a phone call on a mobile phone of a user (stage 210). For example, the mobile phone may be like mobile phone 80 described above with respect to FIG. 1.

According to some embodiments, method 200 may include determining whether the user speaks directly to the mobile phone (stage 220). For example, stage 220 may be performed by an operating system of the mobile phone.

In some embodiments, when the user speaks directly to the mobile phone, method 200 may include acquiring at least one sensor signal by at least sensor mounted within the mobile phone of the user (stage 230). For example, the at least one sensor signal may be at least one sensor signal 102 and the at least one sensor may be at least one sensor 82 described above with respect to FIG. 1. In other embodiments, when the user does not speak directly to the mobile phone, method 200 may move to stage 210.

According to some embodiments, method 200 may include detecting an end of the phone call (stage 240).

According to some embodiments, method 200 may include uploading the at least one acquired sensor signal to a system (stage 250). For example, the at least one acquired sensor signal may be uploaded to a system for determining a change of cognitive capability of a user (e.g., such as system 100 described above with respect to FIG. 1).

In some embodiments, upon uploading of the at least one signal to the system, method 200 may further move to stage 210.

Figure 3A:
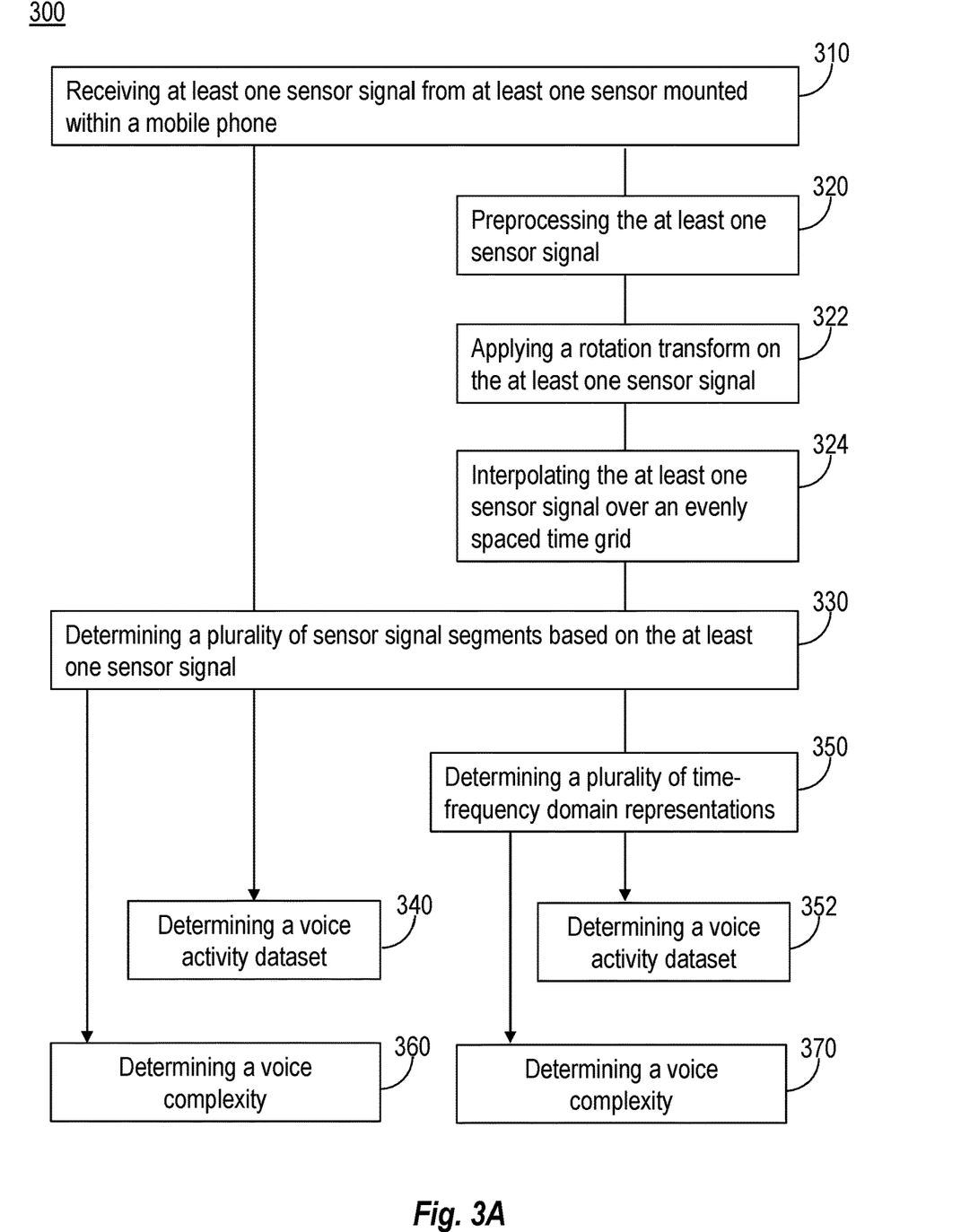
FIG. 3A is a schematic illustration of a method of determining a voice activity dataset, according to some embodiments of the invention.

Reference is now made to FIG. 3A, which is a schematic illustration of a method 300 of determining a voice activity dataset, according to some embodiments of the invention.

Method 300 may be implemented by a voice activity detection module (such as voice activity detection module 120 of system 100 described above with respect to FIG. 1), which may be configured to implement method 200. For example, the voice activity detection module may include a computer processor and non-transitory computer readable medium, wherein the non-transitory computer readable medium may include one or more sets of instructions that when executed cause the computer processor to implement functions/acts described with respect to FIG. 3A.

It is noted that method 300 is not limited to the flowcharts illustrated in FIG. 3A and to the corresponding description. For example, in various embodiments, method 300 needs not move through each illustrated box or stage, or in exactly the same order as illustrated and described.

According to some embodiments, method 300 may include receiving at least one sensor signal acquired by at least one sensor mounted within a mobile phone of a user (stage 310).

For example, the at least one signal may be at least one signal 102, the at least one sensor may be at least one sensor 82 and the mobile phone may be mobile phone 80 described above with respect to FIG. 1. The at least one sensor may be any sensor the readings of which may be affected by a voice of the user, excluding a microphone. For example, the at least one sensor may include at least one of: an accelerometer, gyro and/or magnetometer (e.g., as described above with respect to FIG. 1).

According to some embodiments, method 300 may include preprocessing the at least one sensor signal to yield at least one preprocessed sensor signal (stage 320).

The at least one sensor signal may, for example, include three components, each corresponding to a different axis of three orthogonal axes of the at least one sensor. In some embodiments, the preprocessing may include applying a rotation transform on the at least one sensor signal (stage 322). The rotation transform may be configured to identify a component of the three components that has the largest variability of its data values as compared to other two components. In various embodiments, the rotation transform may be performed by applying a principal component analysis or an independent component analysis on the at least one signal.

The at least one sensor signal that is acquired by the at least one sensor mounted within the mobile phone may have data values that may be irregularly sampled over unevenly spaced time grid. In some embodiments, the preprocessing may include interpolating data values of the at least one sensor signal over a predetermined evenly spaced time grid (stage 324). The interpolation thereof may be based on/performed according to the sampling frequency of the at least one sensor.

According to some embodiments, method 300 may include determining a plurality of sensor signal segments based on the at least one sensor signal (or optionally based on the at least one preprocessed sensor signal) (stage 330).

A time duration of each of the plurality of sensor signal segments and/or an overlap between subsequent sensor signal segments may be determined based on for example, a sampling frequency of the at least one sensor. For example, for the sampling rate of 100 Hz (e.g., typically sampling rate of sensors mounted within mobile phones), the time duration of sensor signal segments may range between 500-800 ms with the overlap of 40-60%.

According to some embodiments, method 300 may include determining a voice activity dataset based on the plurality of sensor signal segments (stage 340). The voice activity dataset may include a plurality of data values. Each of the data values of the voice activity dataset may represent a specific time window (e.g., a time window during the phone conversation) and indicate a voice detection or an absence thereof at the specific time window.

According to some embodiments, method 300 may include determining a voice complexity based on the plurality of sensor signal segments (stage 360).

According to some embodiments, method 300 may include determining a time-frequency domain representation of each of the plurality of sensor signal segments to yield a plurality of time-frequency domain representations (stage 350).

The time-frequency domain representations of each of the sensor signal segments may be performed by, for example, applying a short-time Fourier transform or a wavelet transform to the respective sensor signal segments.

The time-frequency domain representation of each of the sensor signal segments may be an image having image dimensions. The image dimensions may depend on the sampling frequency of the at least one sensor. For example, for the sampling frequency of 100 Hz and sensor signal segment of 500 ms, the image dimensions may be 50×50 pixels.

In some embodiments, method 300 may further include determining the voice activity dataset based on the plurality of the time-frequency domain representations (stage 352).

The voice activity dataset may be determined using one or more machine learning algorithms. For example, the voice activity dataset may be determined using a convolution deep neural network or a recurrent deep neural network (possibly with long short-term memory hidden layers).

The machine learning algorithms may be configured to determine, for each of the plurality of sensor signal segments, or for each of the plurality of time-frequency domain representations thereof, if the respective signal segment or the respective time-frequency domain representation thereof corresponds to a voice or a since segment during the phone conversation of the user, and to output the voice activity dataset.

The machine learning algorithms may be trained based on sensor signals acquired by the at least one sensor mounted within the mobile phone and based on voice recordings acquired by a microphone mounted within the mobile phone. The voice recordings may be analyzed using, for example, standard voice activity detection algorithms. Outputs of the voice activity detection algorithms may be used for training of the machine learning algorithms together with the sensor signals from the at least one sensor. It is noted that voice recordings may be required, in some embodiments, only for training of the machine learning algorithms.

According to some embodiments, method 300 may include determining a voice complexity based on based on the plurality of the time-frequency domain representations (stage 370).

According to some embodiments, method 300 may be applied on two or more sensor signals acquired by two or more sensors (which are not microphones) mounted within the mobile phone of the user. Application of method 300 on two or more sensor signals acquired by two or more sensors may, in some embodiments, improve an accuracy of the determination of voice activity dataset. For example, FIG. 3B shows an example of method 300 as applied on three sensor signals 301 acquired by three different sensors of the mobile phone.

Figure 3B:
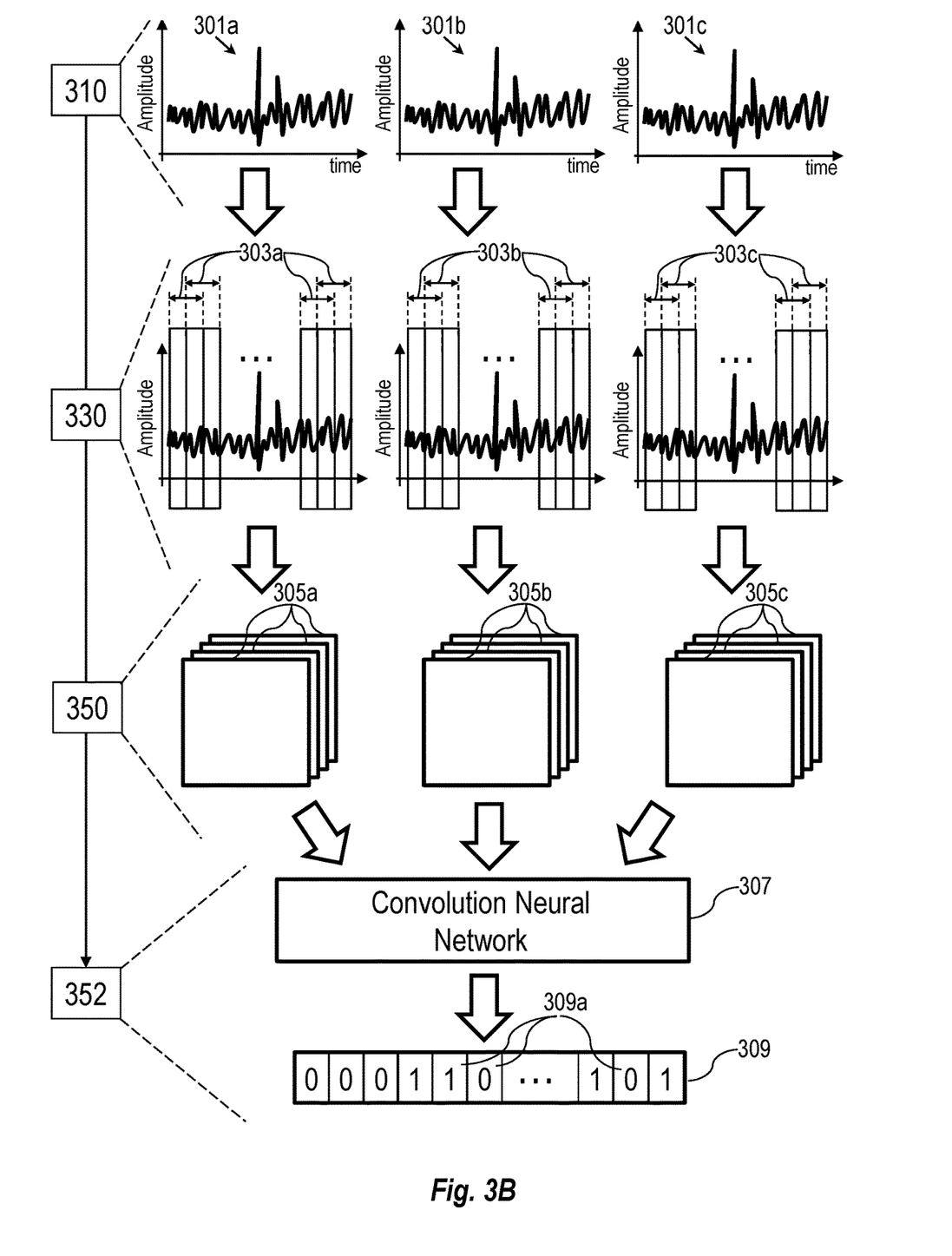
FIG. 3B shows an example of a method of determining a voice activity dataset as applied on three signals, according to some embodiments of the invention.

Reference is now made to FIG. 3B, which shows an example of a method 300 of determining a voice activity dataset as applied on three signals 301, according to some embodiments of the invention.

Figure 3C:
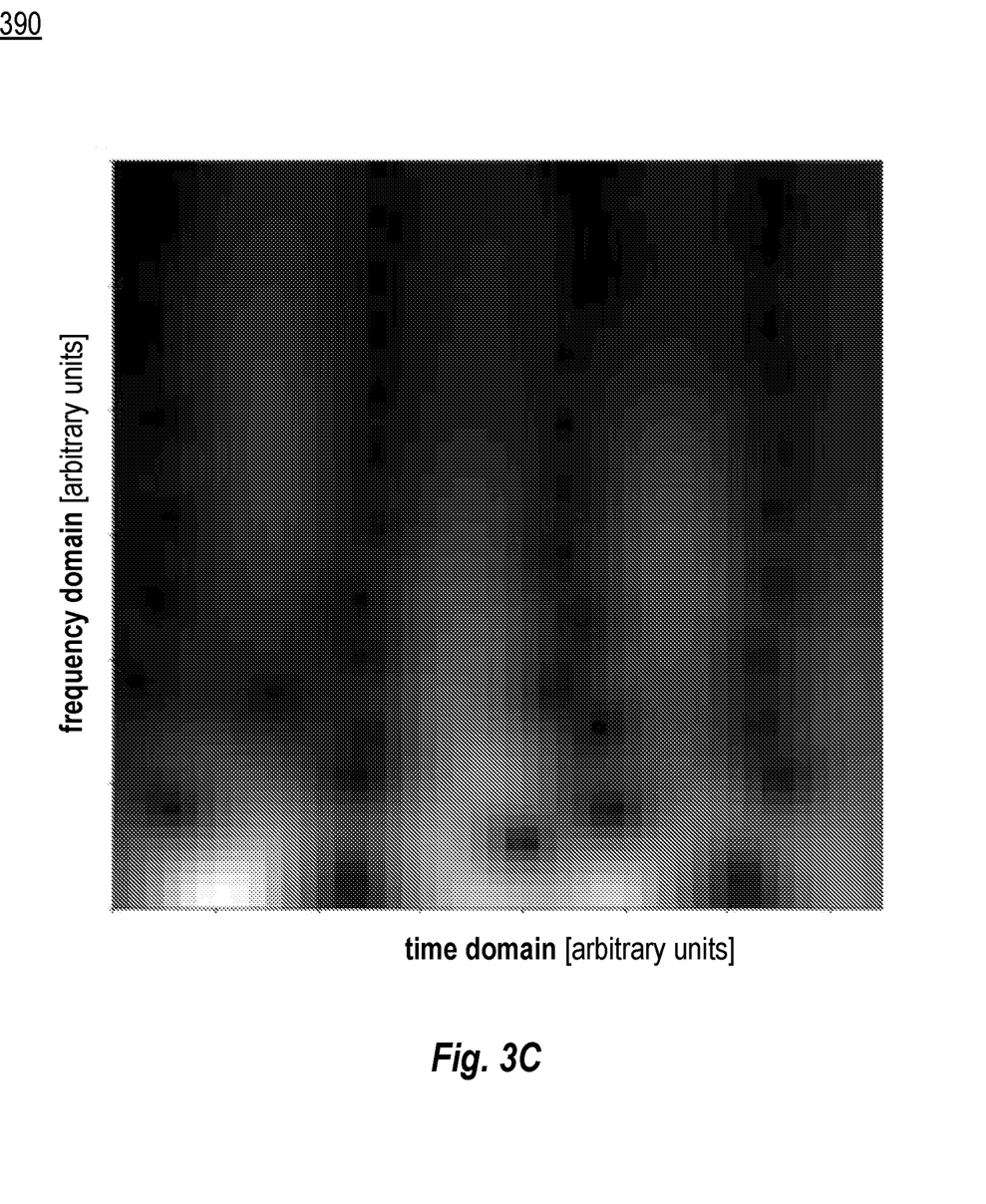
FIG. 3C shows an image of a time-frequency domain representation a sensor signal segment of a sensor signal, according to some embodiments of the invention.

Reference is also made to FIG. 3C, which shows an image of a time-time-frequency domain representation 390 a sensor signal segment of a sensor signal, according to some embodiments of the invention.

According to some embodiments, method 300 may include receiving three signals 301—a first sensor signal 301a from a first sensor, a second sensor signal 301b from a second sensor and a third sensor signal 301c from a third sensor (stage 310) (e.g., as described above with respect to FIG. 3A).

The first sensor, the second sensor and the third sensor may be mounted within the mobile phone of the user and may be like sensor(s) 82 described above with respect to FIG. 1. For example, the first sensor may be an accelerometer sensor, the second sensor may be a gyro sensor and the third sensor may be a magnetometer sensor. The first sensor signal, the second sensor signal and the third sensor signal may be like sensor signals 102 described above with respect to FIG. 1.

According to some embodiments, method 300 may optionally include preprocessing signals 301 (not shown in FIG. 3B but described above with respect to FIG. 3A).

According to some embodiments, method 300 may include determining a first plurality of sensor signal segments 303a for first sensor signal 301a, a second plurality of sensor signal segments 303b for second sensor signal 301b and a third plurality of sensor signal segments 303c for first sensor signal 301c (stage 330) (e.g., as described above with respect to FIG. 3A).

According to some embodiments, method 300 may include determining a first plurality of time-frequency domain representations 305*a* based on first plurality of sensor signal segments 303*a*, a second plurality of time-frequency domain representations 305*b* based on first plurality of sensor signal segments 303*b* and a third plurality of time-frequency domain representations 305*c* based on third plurality of sensor signal segments 303*c* (stage 350) (e.g., as described above with respect to FIG. 3A). For example, FIG. 3C shows an image of a time-frequency domain representation 390 of one of the sensor signals segments of one of the sensor signals.

According to some embodiments, method 300 may include determining voice activity dataset 309 based on first plurality of time-frequency domain representations 305*a*, second plurality of time-frequency domain representations 305*b*, third plurality of time-frequency domain representations 305*c* and using a convolution neural network 307 (stage 352) (e.g., as described above with respect to FIG. 3A). Convolution network 307 may, for example, include hidden layers such as convolutional layers, activation function, pooling layers, fully connected layers and/or normalization layers (not shown in FIG. 3B but well known in the art).

Voice activity dataset 309 may include a plurality of binary data values 309*a*. Each of data values 309*a* of voice activity dataset 309 may represent a specific time window (e.g., a time window during the phone conversation) and indicate a voice detection or an absence thereof at the specific time window.

Figure 4:
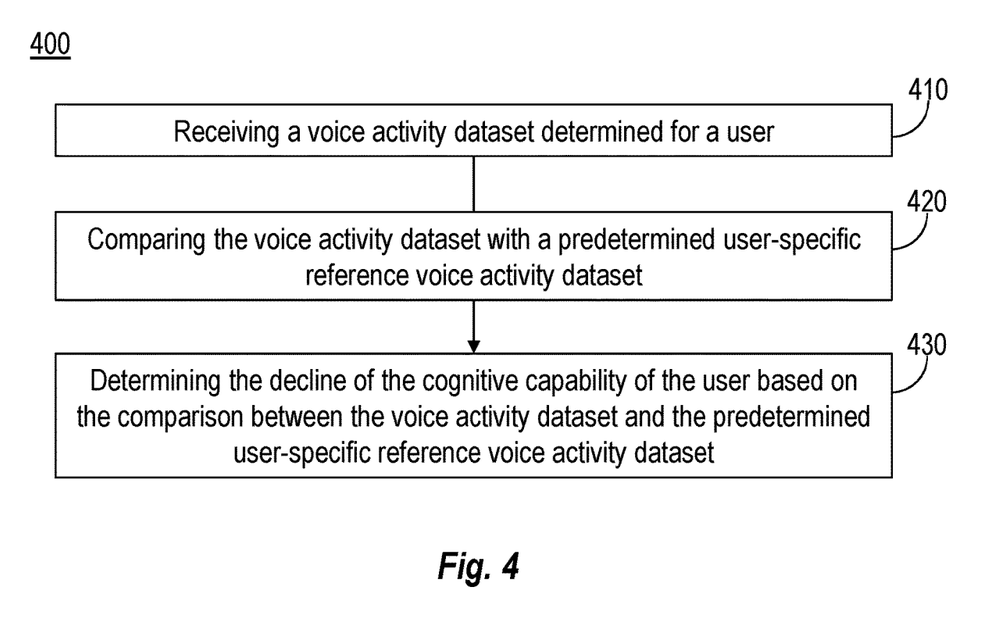
FIG. 4 is a schematic illustration of a method of determining a change of a cognitive capability of a user based on a voice activity dataset of the user, according to some embodiments of the invention.

Reference is now made to FIG. 4, which is a schematic illustration of a method 400 of determining a change of a cognitive capability of a user based on a voice activity dataset of the user, according to some embodiments of the invention.

Method 400 may be implemented by a cognitive capability determination module (such as cognitive capability determination module 130 of system 100 described above with respect to FIG. 1), which may be configured to implement method 400. For example, the cognitive capability determination module may include a computer processor and non-transitory computer readable medium, wherein the non-transitory computer readable medium may include one or more sets of instructions that when executed cause the computer processor to implement functions/acts described with respect to FIG. 4.

According to some embodiments, method 400 may include receiving a voice activity dataset determined for a user (stage 410). The voice activity dataset may be like the voice activity dataset described above with respect to FIGS. 1, 3A and 3B. The voice activity dataset may be determined for the user based on the at least one sensor signal acquired by the at least one sensor (that is not microphone) mounted within the mobile phone of the user, during the phone conversation of the user (e.g., as described above with respect to FIGS. 1 and 2).

According to some embodiments, method 400 may include comparing the voice activity dataset with a predetermined user-specific reference voice activity dataset (stage 420).

The user-specific reference voice activity dataset may, for example, include a voice activity baseline that may be determined, in some embodiments, during first weeks of utilizing method 400.

In some embodiment, the voice activity baseline may be determined based on population-based baseline (either general population or age/condition segmented population). In other embodiments, the voice activity baseline can also be generated by other means, such as phone conversations of the user with care providers, etc.

According to some embodiments, method 400 may include determining the change of the cognitive capability of the user based on the comparison between the voice activity dataset and the predetermined user-specific reference voice activity dataset (stage 430).

In some embodiments, method 400 may include determining one or more changes of the voice activity dataset with respect to the predetermined user-specific reference voice activity dataset that may be indicative of the change of the cognitive capability and thereby determine the change of the cognitive capability of the user.

For example, for a user that has been diagnosed with early stage of Alzheimer's disease, the voice activity baseline may be determined by the recordings of the first weeks (or even before the disease was detected). As the disease progresses and the patent's cognitive ability changes (on scale of months), the system will detect growing difference in the patent's voice activity patterns when compared to the baseline.

Figure 5:
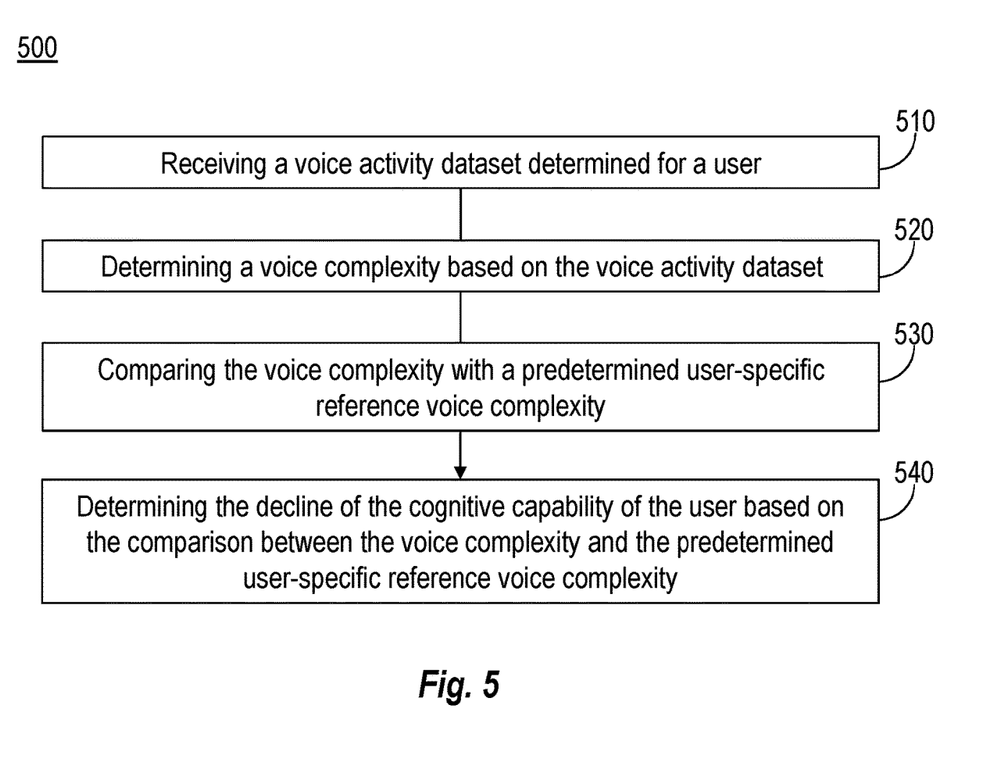
FIG. 5 is a schematic illustration of a method of determining a change of a cognitive capability of a user based on a voice complexity the user, according to some embodiments of the invention.

Reference is now made to FIG. 5, which is a schematic illustration of a method 500 of determining a change of a cognitive capability of a user based on a voice complexity the user, according to some embodiments of the invention.

Method 500 may be implemented by a voice complexity determination module and a cognitive capability determination module (such as voice complexity determination module 140 and cognitive capability determination module 130 of system 100 described above with respect to FIG. 1), which may be configured to implement method 500. For example, the voice complexity determination module and the cognitive capability determination module may include a computer processor and non-transitory computer readable medium, wherein the non-transitory computer readable medium may include one or more sets of instructions that when executed cause the computer processor to implement functions/acts described with respect to FIG. 5.

According to some embodiments, method 500 may include receiving a voice activity dataset determined for a user (stage 510). The voice activity dataset may be like the voice activity dataset described above with respect to FIGS. 1, 3A and 3B. The voice activity dataset may be determined for the user based on the at least one sensor signal acquired by the at least one sensor (that is not microphone) mounted within the mobile phone of the user, during the phone conversation of the user (e.g., as described above with respect to FIGS. 1 and 2).

According to some embodiments, method 500 may include determining a voice complexity based on the voice activity dataset (stage 520). For example, by the voice complexity determination module as described above with respect to FIG. 1.

According to some embodiments, method 500 may include comparing the voice complexity with a predetermined user-specific reference voice complexity (stage 530).

The user-specific reference voice complexity may, for example, include a complexity baseline that may be determined, in some embodiments, during first weeks of utilizing method 400. In some embodiments, the complexity baseline may be determined based on population-based baseline (either general population or age/condition segmented population). In other embodiments, the complexity baseline can also be generated by other means, such as phone conversations of the user with care providers, etc.

According to some embodiments, method 500 may include determining the change of the cognitive capability of the user based on the comparison between the voice complexity and the predetermined user-specific reference voice complexity (stage 540).

In some embodiments, method 500 may include determining one or more changes of the voice complexity with respect to the predetermined user-specific reference voice complexity that may be indicative of the change of the cognitive capability and thereby determine the change of the cognitive capability of the user.

Advantageously, the disclosed systems and methods may enable determining anomalies and trends in the cognition of the user based on the sensor(s) mounted within the mobile phone of the user, without collecting and/or recording the voice of the user.

Embodiments of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A system for determining a change of cognitive capability of a user, the system comprising:
  a storage module configured to receive at least one sensor signal acquired by at least one sensor during a phone conversation of the user, wherein the at least one sensor is mounted within a mobile phone of the user and selected from a group consisting of: an accelerometer, gyro and magnetometer, and wherein the at least one sensor does not include a microphone;
  a voice activity determination module configured to:
    for each of a plurality of sensor signal segments of the at least one sensor signal, determine a time-frequency domain representation, wherein each time-frequency domain representation comprises an image, the image having dimensions depending on a sampling frequency of the at least one sensor;
    determine a voice activity dataset, wherein the voice activity dataset comprises a plurality of data values each representing a specific time window and indicating a voice detection or an absence thereof at the time window thereof, wherein the voice activity dataset is determined based on one or more of the time-frequency domain representations using a machine learning algorithm, the machine learning algorithm trained using one or more outputs of a voice activity detection algorithm;

a voice complexity determination module configured to determine a voice complexity based on one or more of the time-frequency domain representations, the voice complexity representing an ability of the user to dynamically change voice patterns by changing the voice pitch, power and space between syllables; and a cognitive capability determination module configured to determine a change of a cognitive capability of the user based on the voice activity dataset and based on the voice complexity.

2. The system of any claim 1, wherein the at least one sensor signal is acquired upon a verification that the user speaks directly to the mobile phone during the phone conversation.

3. The system of claim 1, wherein the voice activity determination module is further configured to:
determine the plurality of sensor signal segments based on the at least one sensor signal; and
determine the voice activity dataset based on the plurality of sensor signal segments.

4. The system of claim 3, wherein:
the cognitive capability determination module is further configured to determine the voice activity dataset based on the plurality of the time-frequency domain representations using the machine learning algorithm.

5. A method of determining a change of cognitive capability of a user, the method comprising:
receiving at least one sensor signal acquired by at least one sensor during a phone conversation of the user, wherein the at least one sensor is mounted within a mobile phone of the user and selected from a group consisting of: an accelerometer, gyro and magnetometer, and wherein the at least one sensor does not include a microphone;
for each of a plurality of sensor signal segments of the at least one sensor signal, determining a time-frequency domain representation, wherein each time-frequency domain representation comprises an image, the image having dimensions depending on a sampling frequency of the at least one sensor;
determining a voice activity dataset, wherein the voice activity dataset comprises a plurality of data values each representing a specific time window and indicating a voice detection or an absence thereof at the time window thereof, wherein the voice activity dataset is determined based on one or more of the time-frequency domain representations using a machine learning algorithm, the machine learning algorithm trained using one or more outputs of a voice activity detection algorithm;
determining a voice complexity based on one or more of the time-frequency domain representations, the voice complexity representing an ability of the user to dynamically change voice patterns by changing the voice pitch, power and space between syllables; and
determining a change of a cognitive capability of the user based on the voice activity dataset and based on the voice complexity.

6. The method of claim 5, further comprising acquiring the at least one sensor signal upon a verification that the user speaks directly to the mobile phone during the phone conversation.

7. The method of claim 5, further comprising:
determining the plurality of sensor signal segments based on the at least one sensor signal; and
determining the voice activity dataset based on the plurality of sensor signal segments.

8. The method of claim 7, further comprising:
determining the voice activity dataset based on the plurality of the time-frequency domain representations using the machine learning algorithm.

* * * * *